United States Patent [19]

Wakatake

[11] Patent Number: 5,183,638
[45] Date of Patent: Feb. 2, 1993

[54] AUTOMATIC IMMUNITY ANALYSIS APPARATUS WITH MAGNETIC PARTICLE SEPARATION

[75] Inventor: Koichi Wakatake, Tokyo, Japan

[73] Assignees: Kabushiki Kaisha Nittec; Mitsui Pharmaceuticals, Inc., both of Tokyo, Japan

[21] Appl. No.: 620,608

[22] Filed: Dec. 3, 1990

[30] Foreign Application Priority Data

| Dec. 4, 1989 | [JP] | Japan | 1-313363 |
| Jan. 19, 1990 | [JP] | Japan | 2-3063 |
| Jan. 24, 1990 | [JP] | Japan | 2-4633 |
| Jan. 24, 1990 | [JP] | Japan | 2-4634 |
| Mar. 16, 1990 | [JP] | Japan | 2-26198 |

[51] Int. Cl.$^5$ .................... G01N 21/01; G01N 21/11; B01F 11/00
[52] U.S. Cl. .................... 422/64; 422/63; 422/67; 422/100; 366/218
[58] Field of Search .......... 422/63, 64, 65, 67, 422/100; 366/217, 218; 436/526

[56] References Cited

U.S. PATENT DOCUMENTS

| Re. 23,634 | 3/1953 | Hewson | 422/67 |
| 2,046,256 | 6/1936 | Fisher | 366/218 X |
| 4,141,954 | 2/1979 | Shigetomi | 422/64 |
| 4,265,855 | 5/1981 | Mandle et al. | 422/65 |
| 4,459,265 | 7/1984 | Berglund | 422/100 X |
| 4,774,055 | 9/1988 | Wakatake et al. | 422/100 X |
| 4,803,050 | 2/1989 | Mack | 422/67 X |
| 4,872,353 | 10/1989 | Orr, Jr. et al. | 422/64 X |

FOREIGN PATENT DOCUMENTS

| 0212663 | 3/1987 | European Pat. Off. | 422/100 |
| 0358948 | 3/1990 | European Pat. Off. | 436/526 |
| 57-110963 | 7/1982 | Japan . | |
| 62-133354 | 6/1987 | Japan . | |
| 62-133355 | 6/1987 | Japan . | |
| 62-133356 | 6/1987 | Japan . | |

Primary Examiner—James C. Housel
Assistant Examiner—Arlen Soderquist
Attorney, Agent, or Firm—Lowe, Price, LeBlanc & Becker

[57] ABSTRACT

An immunity analysis apparatus for use with magnetic particles in which a sample is transferred to a reaction vessel and the reaction vessel is conveyed past several devices for adding and agitating a magnetic particle solution, adding a stroma solution, absorbing the particles to an inner wall of the reaction vessels to remove the reaction solution, adding an enzyme labelling antibody solution, absorbing the particle on an inner wall a second time to remove the resulting solution, adding a stop solution, measuring the result, and cleaning the reaction vessels for a reuse. The device additionally has structure for agitating the magnetic particle reagent solution containers and moving a pipet arm independent of an L-shaped agitating rod arm during a portion of its movement to supply the reaction vessels with the magnetic particle solution.

4 Claims, 8 Drawing Sheets

AUTOMATIC IMMUNITY ANALYSIS APPARATUS WITH MAGNETIC PARTICLE SEPARATION

SCOPE OF THE TECHNOLOGY

The present invention relates to an automatic immunity analysis apparatus and particularly to the automatic immunity analysis apparatus appropriate to the oxygen immunity measurement method (hereinafter referred to as the EIA method) using the antigen-antibody reaction.

BACKGROUND OF THE TECHNOLOGY

The EIA method has been used recently as a method to measure immunity using the antigen-antibody reaction, as known in the prior art.

The reaction of the EIA method is so sensitive and accurate that the method is used to analyze, for example, CEA, Fer, $\beta_2$-M, IgE, TSH, $T_3$, $T_4$, AFP, CA-50, etc.

Such EIA method as described above is classified into the beads EIA method and coating EIA method, etc. as known in the prior art; in the former, antibody is sensitized on the surface of spherical beads while it being coated on the wall surface of cells in the latter.

However, in these EIA methods known in the prior art, it is required to add an antibody non-solution, stroma solution, reaction stop solution, etc. in time according to the progress of reaction. Such a work of adding them is much complicated. Moreover, the reaction time of such an inspection is so long as a long time is spent until a final inspection result is available. These problems associated with conventional EIA methods are disadvantageous for practical applications.

DISCLOSURE OF THE INVENTION

In order to solve the problems associated with conventional technologies, an object of the present invention is to offer an automatic immunity analysis apparatus comprising reaction vessels arranged in a series, a conveying means for said reaction vessels, a first dividing means which sucks a sample in a predetermined quantity at a predetermined position and divides and charges said sample into each of said vessels, a first agitating means which divides and charges an antibody insoluble magnetic solution into each of said reaction vessels containing said sample divided and charged, a second dividing means which is equipped after said first agitating means and divides and charges a stroma solution into each of said vessels, an adsorbing means which makes said antibody insoluble magnetic solution adsorbed onto an inner wall surface of each of said reaction vessels, a first cleaning means which discards a reaction solution out of each of said reaction vessels while said antibody insoluble magnetic solution is still adsorbed on the inner wall of each of said reaction vessels, and then cleans each of said vessels, a second agitating means which divides and agitates an enzyme labeling antibody solution, a second adsorbing means which makes said antibody insoluble magnetic solution adsorbed onto an inner wall surface of each of said reaction vessels, a second cleaning means which discards a reaction solution out of each of said reaction vessels while said antibody insoluble magnetic solution is still adsorbed on the inner wall of each of said reaction vessels, and then cleans each of said vessels, a third dividing means which divides and charges a reaction stop solution, a measuring means which optically measures a sample in each of said reaction vessels at an optical measuring position, and a third cleaning means which cleans the inside of each of said reaction vessels after completion of a measurement.

Another aspect of the present invention is to provide the automatic immunity analysis apparatus specified above, in which said first agitating means for an antibody insoluble magnetic solution comprises a reagent vessel holder which is rotated by means of a driving apparatus, a rotating body which is engaged with a retention hole of said reagent vessel holder in a freely rotatable manner, a fixed gear body on a peripheral surface of which gear teeth are cut, a gear body which engages with the gear teeth of said fixed gear body and drives said rotating body when said reagent vessel holder rotates, and protrusion bodies which are elevated in predetermined intervals along a peripheral surface of said fixed gear body, wherein an antibody insoluble magnetic solution accommodation in said rotating body is rotated and agitated when said reagent vessel holder revolves, and accommodated in said rotating body in such a manner that said reagent antibody insoluble magnetic solution is shaken and agitated with one of said protrusion bodies.

Still another object of the present invention is to create the automatic immunity analysis apparatus specified in the first object above for the present invention, in which said first agitating means that divides and charges an antibody insoluble magnetic solution contained in each of said reagent vessel into each of said reaction vessels comprises an agitating rod arm and a pipet arm, where said agitating rod arm is equipped with one of said agitating bodies at an intermediate portion and a draining pipet bearingly supported at a top portion and shaped into a substantial L plane, and said pipet arm is equipped with a dividing pipet at an end portion, while said agitating pipet at an end portion, while said agitating rod arm and said pipet arm being bearingly and coaxially supported; wherein said agitating rod, said draining pipet and said dividing pipet are cleaned at a predetermined position; then only said dividing pipet rotates while pushing the draining pipet and moves to a solution sucking position; and said draining pipet returns back in place when said dividing pipet sucks the antibody insoluble magnetic solution and returns back to said cleaning position.

According to still another object of the invention, an automatic immunity analysis apparatus realized by the invention is the automatic immunity analysis apparatus specified in the first object above of the present invention, in which said first and second cleaning means to clean the inner walls of said reaction vessels comprise a substantially L-shaped arm fixed onto a shaft at an end, a solution suction pipet mounted at a top portion of said arm, a cleaning-water supplying pipet and an agitating body; wherein said solution suction pipet, said cleaning-water supplying pipet and said agitating body are mounted at a top portion of said arm in such a sequential order as form a downstream side to an upstream side in the direction of conveying the reaction vessels into which said pipets and said agitating body are inserted.

BRIEF DESCRIPTION OF THE DRAWINGS

FIGS. 9 (A) through (C) are descriptive plan views sequentially showing the operation of the draining pipet device, the third pipet device and the agitating device of FIG. 7.

PREFERRED EMBODIMENTS OF THE PRESENT INVENTION

The automatic immunity analysis apparatus A as shown in the drawings relates to the 2 step type.

The 2 step type in this specification is defined by a system in which, before an enzyme labeling antibody solution is charged into a reaction vessel, the vessel is cleaned to remove a residual antibody insoluble magnetic solution. The 1 step type is a system with such a cleaning process as in the 2 step type is omitted.

Figure 1:
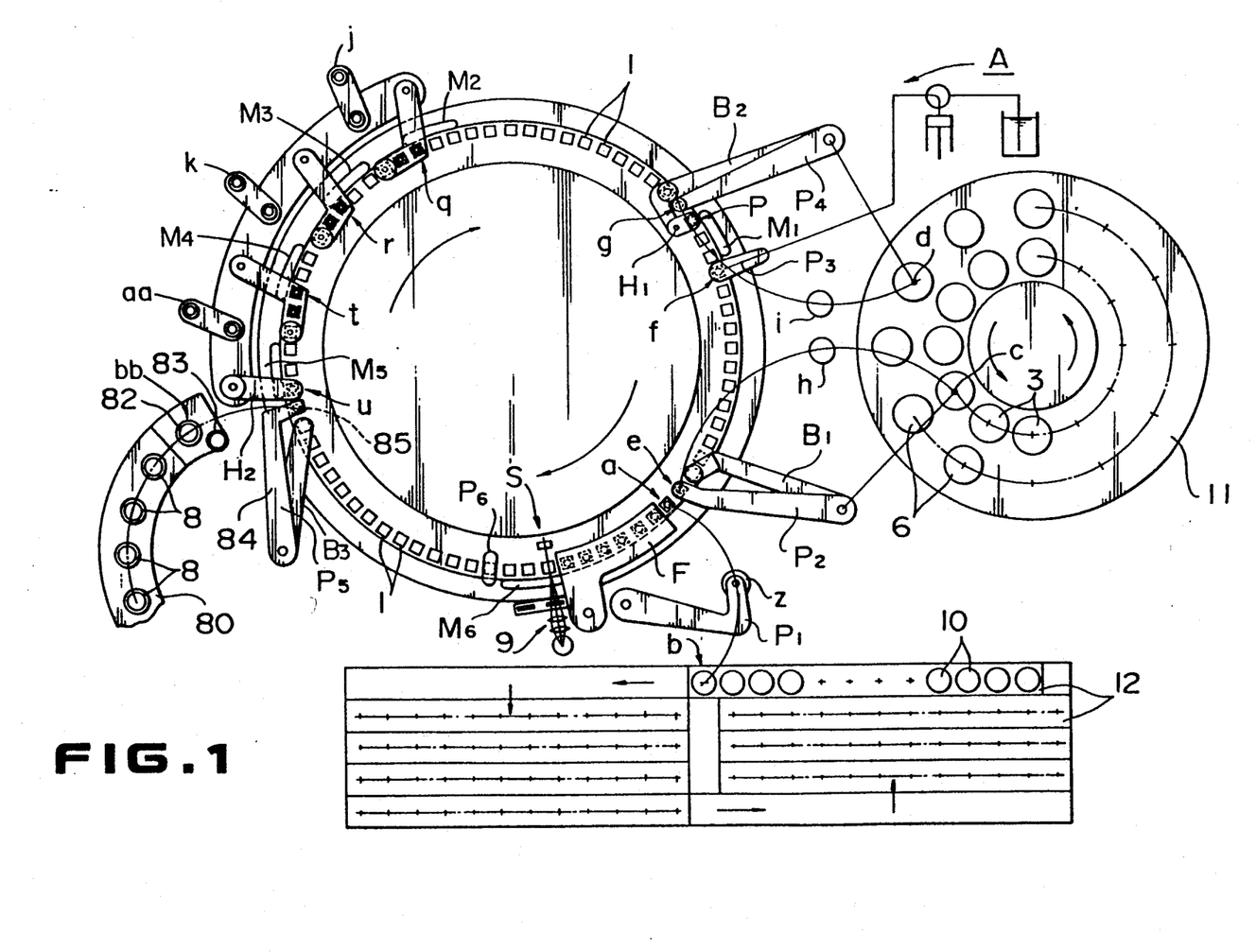
FIG. 1 is a plan view generally showing the entire composition of an embodiment of the automatic immunity analysis apparatus according to the present invention.
Figure 11:
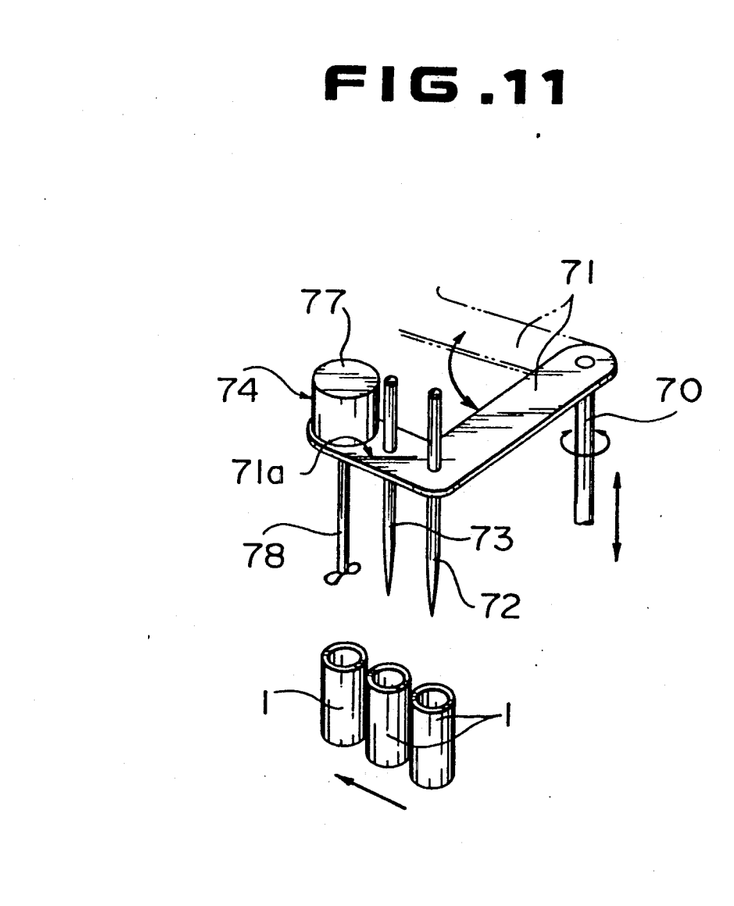
FIG. 11 is an oblique view showing the composition of the cleaning and agitating device of FIG. 10.
Figures 12, 13:
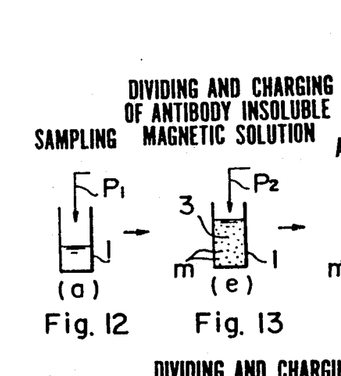
FIGS. 12-34 show a flowchart sequentially showing operating processes of an automatic immunity analysis apparatus according to the embodiment of the present invention.
Figures 14, 15:
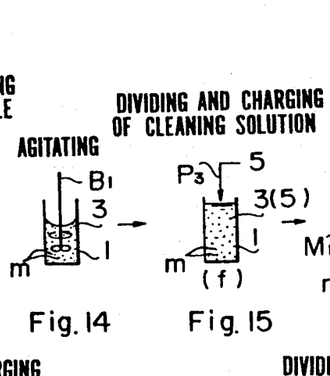
Figures 16, 17, 18:
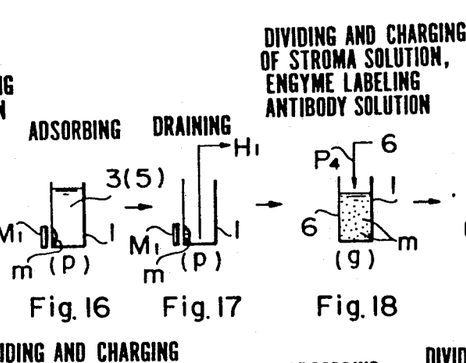
Figure 19:
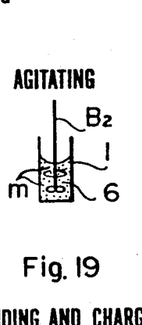
Figures 20, 21, 22, 23, 24, 25, 26, 27, 28, 29, 30, 31, 32, 33, 34:
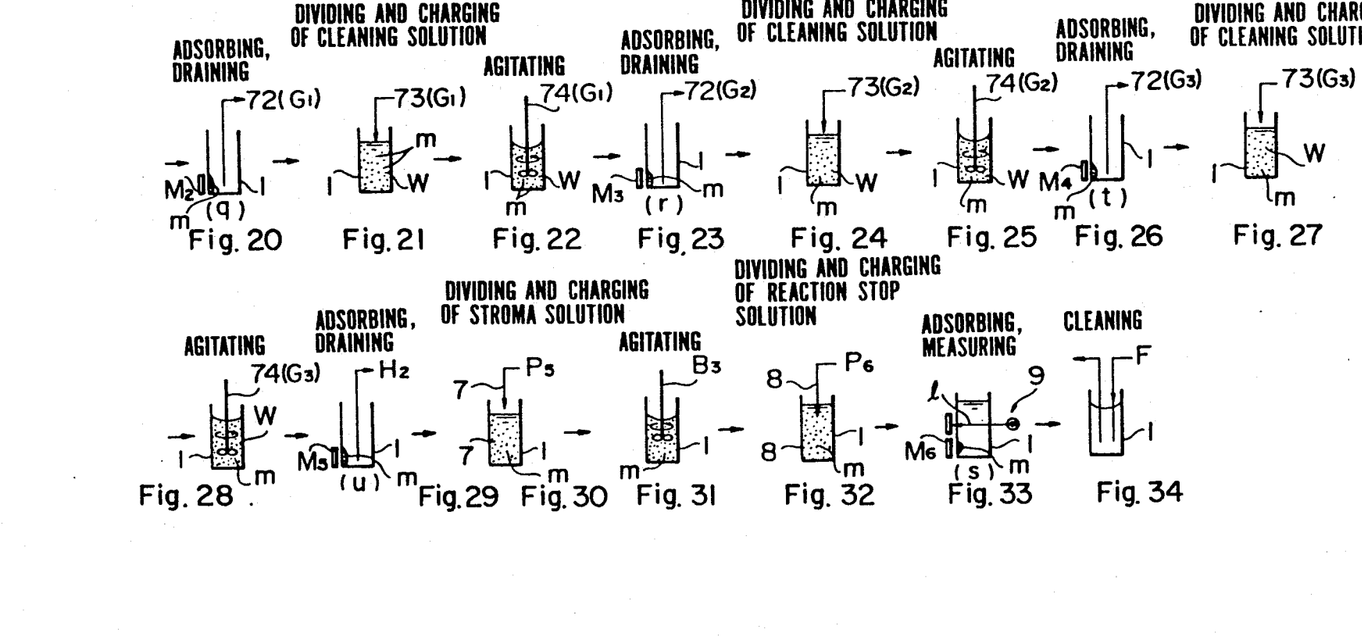

Referring to FIG. 1, the embodiment of an automatic immunity analysis apparatus A comprises a plurality (72 pieces in this embodiment) of reaction vessels 1 arranged in a loop shape, a driving apparatus to convey said reaction vessels 1, a sampling pipet device P1 which sucks a predetermined quantity of a sample at a sampling position b and divides and charges the sample into one of said reaction vessels 1, which is set at a position "a," a first pipet device P2 that divides and charges an antibody insoluble magnetic solution into the reaction vessel filled with said sample, an agitating device B1 that agitates the divided and charged antibody insoluble magnetic solution in the reaction vessel 1, a second pipet device P3 that divides and charges a cleaning solution 5 into the reaction vessel 1, a first magnetic body M1 that makes an antibody insoluble magnetic body m, see FIGS. 11 and 17 adsorbed on the inner wall surface of the reaction vessel 1 in which the cleaning solution 5, see FIG. 15 has been additionally divided and charged, a draining pipet device H1 that sucks and discards the antibody insoluble magnetic solution in the reaction vessel 1 while the antibody insoluble magnetic body m still being adsorbed on the inner wall surface of the reaction vessel 1, a third pipet device P4 that divides and charges a stroma solution, i.e., an enzyme labeling antibody in reagent vessel solution 6 into said reaction vessel 1 after completion of sucking and discarding with the draining pipet device H1, an agitating device B2 that agitates the divided and charged stroma solution, i.e. enzyme labeling antibody solution in the reaction vessel 1, magnetic bodies M2, M3, M4 and M5 that make said antibody insoluble magnetic body adsorbed on the inner wall surface of the reaction vessel 1 after completion of agitating with the agitating device B2 and a magnetic body M6 located at an optical measuring position s, cleaning and agitating devices G1 through G3 that suck and discard the antibody insoluble magnetic solution in the reaction vessel 1 while the antibody insoluble magnetic body m still being adsorbed on the inner wall surface of the reaction vessel 1 while also supplying a cleaning solution into the reaction vessel 1 from which said antibody insoluble magnetic solution has been discarded and agitating the cleaning solution now charged in the reaction vessel 1, a fourth pipet device P5 that divides and charges a stroma solution into the reaction vessel 1 after completion of agitating with the cleaning and agitating devices G1 through G3, an agitating device B3 that agitates the divided and charged stroma solution in the reaction vessel 1, a fifth pipet device P5 that divides and charges a reaction stop solution in vessel 8 after completion of agitating with the agitating device B3, an optical measuring device 9 that optically measures the reaction state of a sample in the reaction vessel 1 at an optical measuring position, an indication device (not illustrated) that indicates an absorbancy measured with the optical measuring device 9 onto a printer or a CRT, etc. after a A/D conversion, and a cleaning device F that cleans the inside of the reaction vessel after completion of measuring.

The driving device for conveying the reaction vessel 1 conveys a plurality of said reaction vessels 1 intermittently pitch after pitch counterclockwise of FIG. 1 sequentially up to a predetermined position while heating up the vessels 1 to a predetermined temperature. The device stepwise rotates in the direction (counterclockwise in FIG. 1) to the direction of conveying intermittently (clockwise in FIG. 1) by a number of steps 1 less than the number of reaction vessels (by 71 steps, i.e. 360°− 360°/72°). As a result, the reaction vessels 1 are intermittently conveyed clockwise in FIG. 1 vessel by vessel. This means to convey the reaction vessels comprises a pulse motor known in the prior art. It is of course possible for the purpose of the present invention that the step rotation control for said 360°-n (number of vessels) is substituted by the step rotation control of 360° +n (number of vessels). At that time, the sample in the reaction vessels 1 is heated up to about 37° C. by a constant temperature device known in the prior art (not illustrated).

At a sampling position "a," a predetermined quantity of the sample is sucked out of a sample vessel 10 and divided and charged into a reaction vessel 1.

12 sample vessels 10 are mounted on a sample cassette 12 and sequentially and linearly conveyed up to a sample suction position b by means of a sample vessel conveying device (not illustrated) comprising a feeding mechanism known in the prior art.

Said antibody insoluble magnetic solution is accommodated in reagent vessels 3 arranged in a loop shape inside a reagent holder 11. Said stroma solution, i.e. enzyme labeling antibody solution is accommodated in reagent vessels 6 arranged in a loop shape inside said reagent holder 11.

At that time, the antibody insoluble magnetic body m of said antibody insoluble magnetic solution precipitates onto the bottom of the vessels if the vessels are placed stationary because of a large specific gravity of the antibody insoluble magnetic body m, resulting in fluctuation in measurement accuracies. To prevent this, the antibody insoluble magnetic solution is agitated using the agitating device 20, see FIG. 2.

Figure 2:
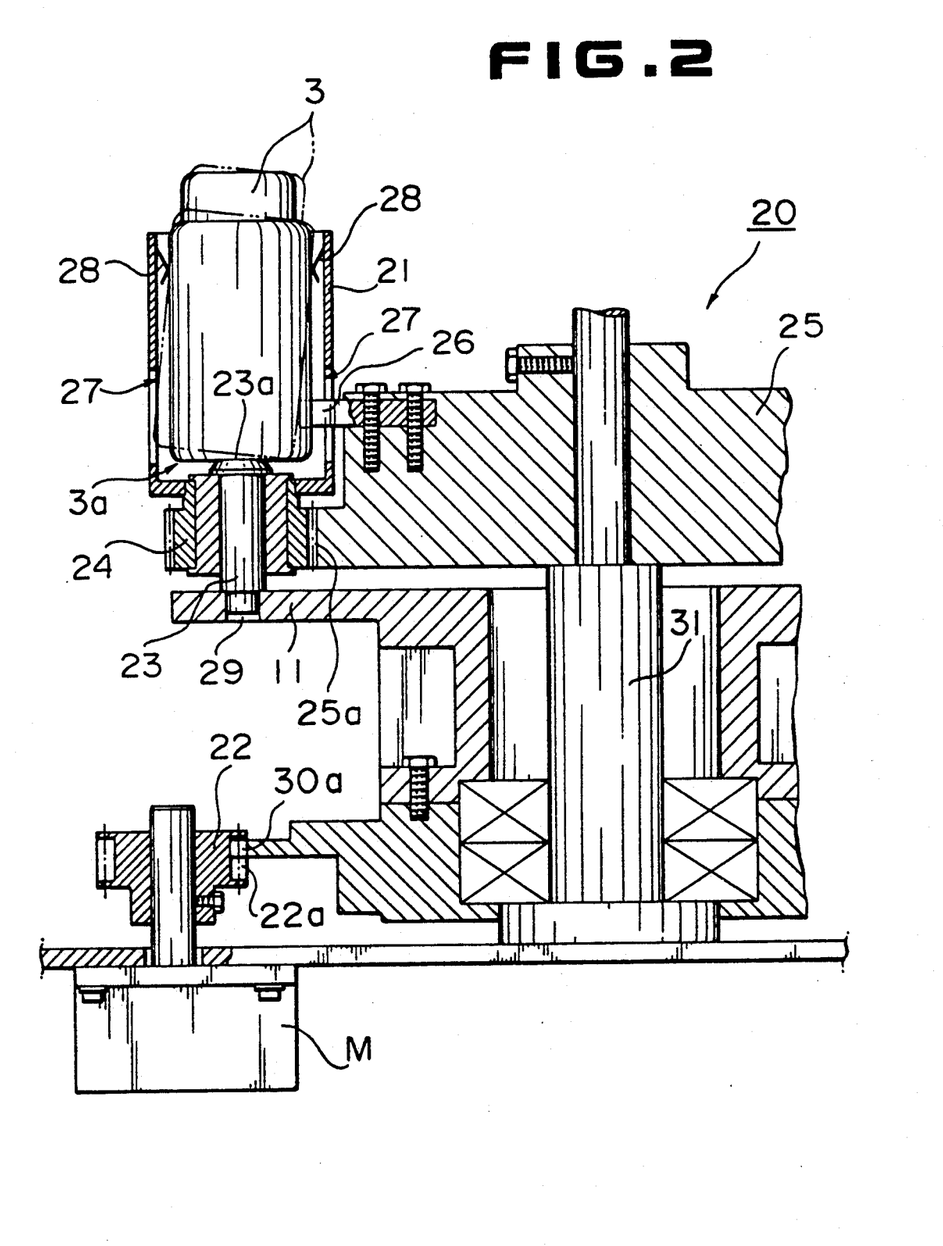
FIG. 2 is a section view that shows the structure of an agitating device to shake and agitate a reagent vessel accommodating an antibody insoluble magnetic solution.

More explicitly, the antibody insoluble magnetic solution encased inside said reagent vessels 3 comprises magnetic fine particles known in the prior art (a diameter of about 2.6 $\mu$m) after fixing as an antibody. In a stationary state, the specific gravity of said antibody insoluble magnetic solution is so large as precipitating onto the bottom portion of reagent vessels 3.

Said reagent holder 11 conveys reagent vessels 3 and 6 accommodating an antibody insoluble magnetic solution and a stroma solution, i.e. enzyme labeling antibody solution respectively up to reagent dividing and charging positions c and d, respectively by means of a driving device not illustrated. When the reagent vessels 3 and 6 accommodating an antibody insoluble magnetic solution and a stroma solution, i.e. enzyme labeling antibody solution arrive at said reagent dividing and charging positions c and d, respectively, said first pipet device P2 and 3rd pipet device P4 suck predetermined quantities of the antibody insoluble magnetic solution and stroma, i.e. enzyme labeling antibody solution and divide and charge said solutions into reaction vessels 1 conveyed to an antibody insoluble magnetic solution dividing and charging position e and enzyme labeling antibody solution dividing and charging position g, respectively. Bottles arranged on said reagent holder 11 are set beforehand at predetermined positions each of which is stored in a control device CPU.

Said agitating device 20 that shakes and agitates reagent vessels 3 accommodating said antibody insoluble magnetic solution is shown in FIGS. 2 through 5 (for the conveniency of description, the illustration of the reagent vessel 6 is omitted among reagent vessels 3 and 6 held in the reagent holder 11). The agitating device 20 comprises a rotating body 21 loosely holding a reagent vessel, said reagent holder 11 in a loop shape while holding a plurality of rotating bodies 21 in a freely rotatable manner in predetermined intervals, a driving device 22 to rotate said reagent holder 11, a supporting body 23 to connect said rotating body 21 and reagent holder 11, a gear body 24 fixed onto the supporting body 23, a fixed gear body 25 with gear teeth 25a that engage with the gear body 24, and protrusion bodies 26 elevated on the outer periphery of the fixed gear body 25 in predetermined intervals.

Figure 3:
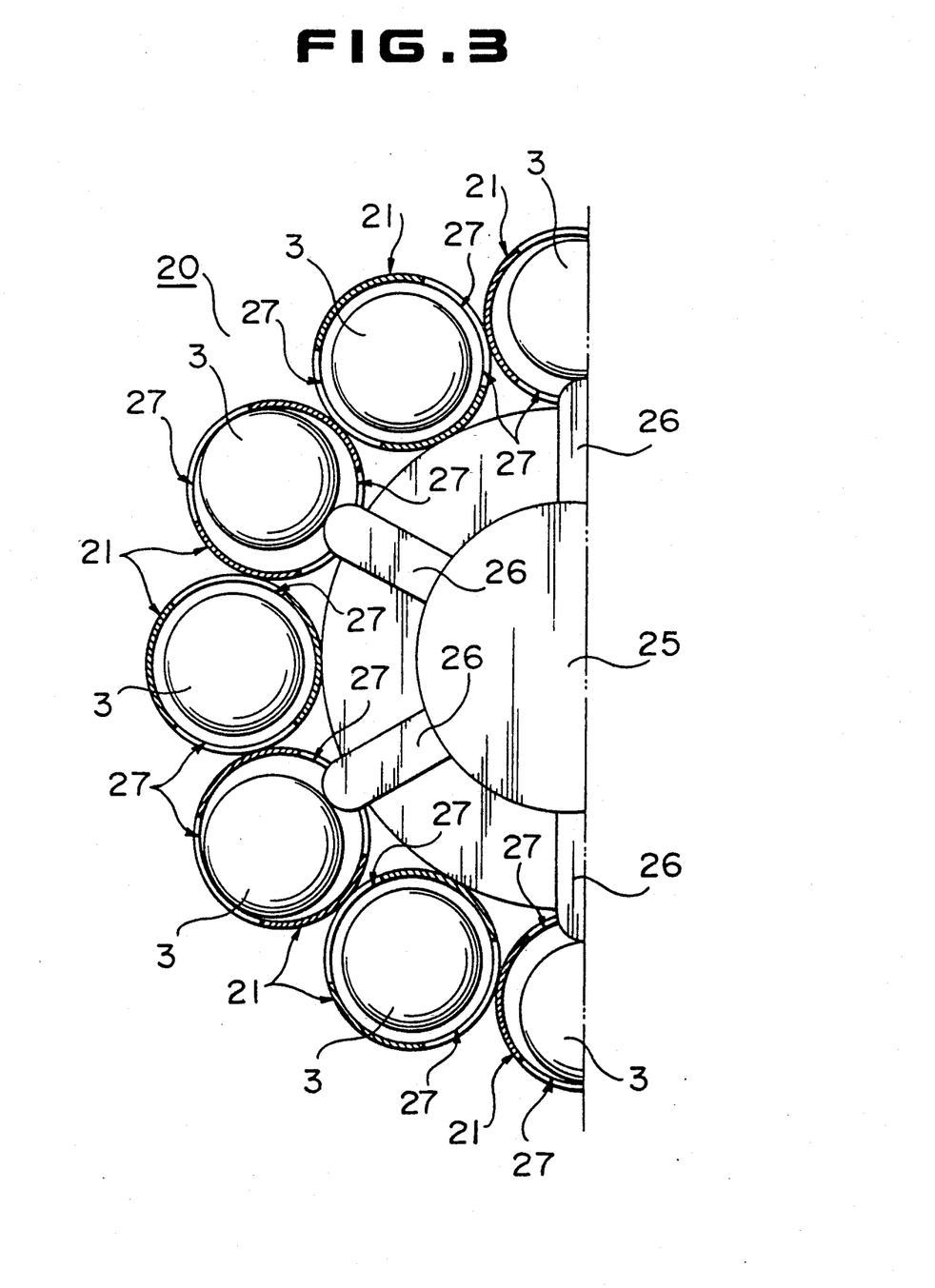
FIG. 3 is a partial cutaway view of the agitating device shown in FIG. 2.
Figure 4:
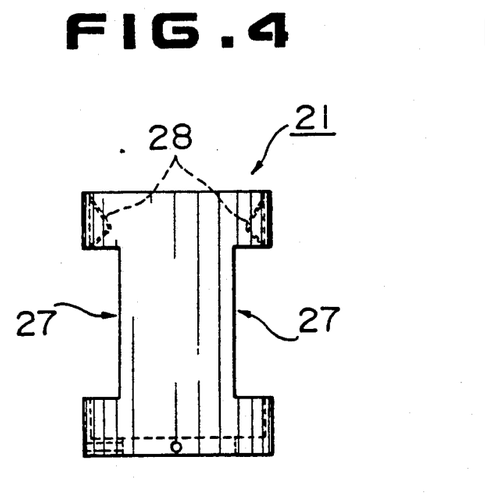
FIG. 4 is a front view that shows the composition of a rotating body.
Figure 5:
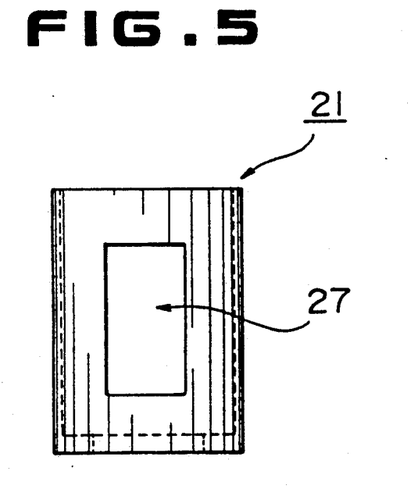
FIG. 5 is a side view showing the composition of said rotating body.

The rotating body 21 is constructed with a U-shaped section of as shown in FIG. 2 and an inner diameter of a vessel accommodation portion 3a slightly larger than the outer diameter of a reagent vessel 3, so that a reagent vessel 3 can swing and move with a predetermined clearance. In a lower periphery of the rotating body 21, two apertures 27 are provided to allow said protrusion body 26 to advance and retract as shown in FIGS. 3 through 5, in angular spacings of 45 degrees each. In addition, in the upper portion of the inner periphery of said rotating body 21, a plurality of spring materials 28 is mounted in predetermined intervals along the inner periphery of the rotating body 21 in order to hold a reagent vessel 3 substantially at a center portion of the rotating body 21, while resiliently contacting with the outer periphery of the reagent vessel 3.

On the bottom portion of said rotating body 21 thus composed, a head portion 23a of said supporting body 23 is protruded in a freely rotatable manner while being in contact with the bottom portion of the reagent vessel 3 accommodated in said rotating body 21. On the outer periphery of said supporting body 23, said gear body 24 fixed on the bottom portion of the rotating body 21 at an upper end portion in a rotatable manner.

The lower end portion of said supporting body 23 is inserted rotatably into a holding hole 29 equipped in said reagent holder 11.

The head portion 23a of said supporting body 23 constructed as described above is composed in such a manner that said reagent vessel 3 is set in the rotating body 21 so that the axial centers of the reagent vessel 3 and the supporting body 23 can naturally coincide while the head portion 23a comes in contact with a center portion of a gentle recess portion of the reagent vessel 3.

The reagent holder 11 is fixed is composed in such a manner as a reagent vessel 3 accommodating an antibody insoluble magnetic solution is conveyed to a predetermined reagent dividing and charging position (not illustrated) by means of a motor M, a gear 22a fixed onto the rotating shaft of the motor M and coming in engagement with gear teeth 30a constructed in a lower portion of the reagent holder 11. When the reagent vessels 3 accommodating the antibody insoluble magnetic solution divided and charged at said reagent dividing and charging position arrives, said first pipet device P2 sucks said antibody insoluble magnetic solution from the reagent vessel 3 at said reagent dividing and charging position by a predetermined quantity and divides and charges the same into the reaction vessel 1. The fixed gear body 25 shaped into a circular disc is fixed on a supporting body 31 as shown in FIG. 2, and arranged inside of said supporting body 23 so that the gear 25a constructed in a lower portion of the outer periphery can normally engage with said gear body 24.

In an upper portion of the outer periphery of said fixed gear body 25, said protrusion bodies 26 are arranged in elevation in predetermined intervals along circumferential direction.

Therefore, the antibody insoluble magnetic solution in the reagent vessel 3 accommodated in the rotating body 21 is rotated and agitated when said gear body 24 engages with the gear 25a of the fixed gear body 25 while the reagent holder 11 being rotated and conveyed to the dividing and charging position as described above. In addition, the reagent vessel 3 accommodated in said rotating body 21 is tilted and shaken within the rotating body 21 when it comes in contact with the protrusion body 26 protruded on the fixed gear body 25 during the rotating and conveying operation described above. Consequently, every time the reagent holder 11 is rotated by the driving device 22, the reagent vessel 3 held by the rotating body 21 is rotated and shaked, thereby the antibody insoluble magnetic solution in said reagent vessel 3 being efficiently shaked and agitated.

Figure 6:
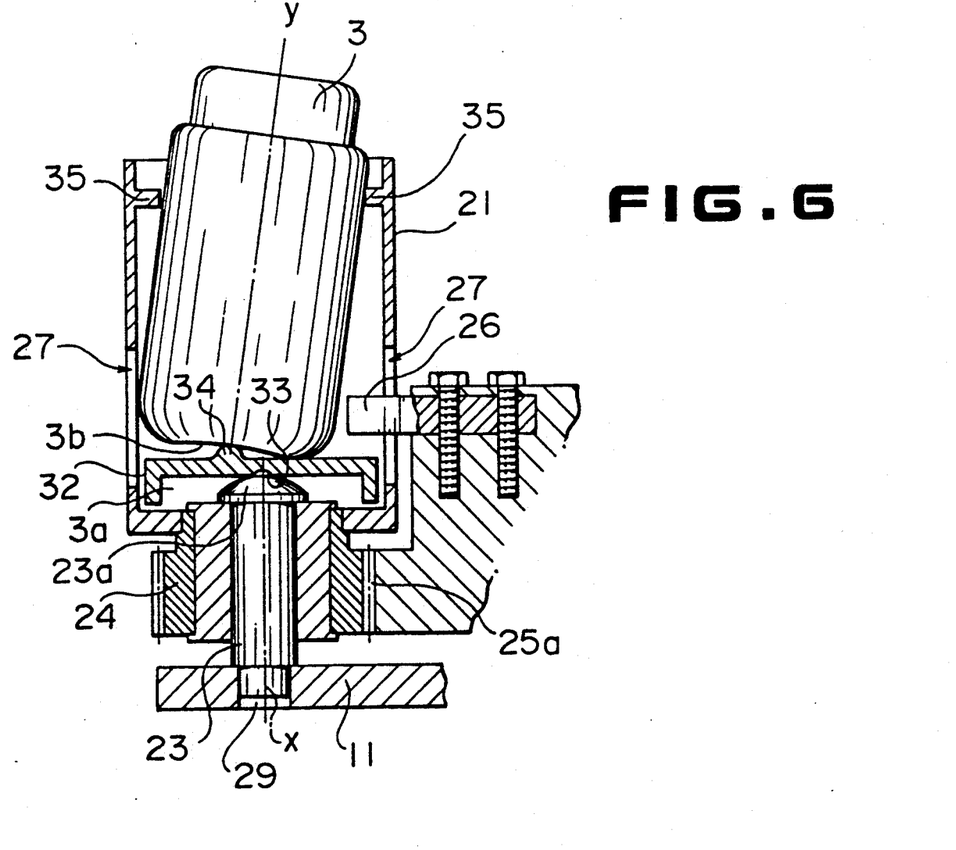
FIG. 6 is a section view that denotes another embodiment of the agitating device to shake and agitate a reagent vessel accommodating an antibody insoluble magnetic solution.

Said agitating device 20 can also be composed in the following manner. Referring to FIG. 6, an axis x of a supporting body 23 supported on the reagent holder 11 in a free rotatable manner is deviated from an axis y of the reagent vessel 3 when it is housed in the rotating body 21. A rotation assistant body 32 is equipped between the head portion 23a of the supporting body 23 and the bottom portion of the reagent portion 3 while engaging the head portion 23a of the supporting body 23 with a recess portion 33 provided at a rotation center portion of said rotation assistant body 32. In addition, a rotation center protrusion 34 is provided in contact with a center portion of a gentle recess portion 3b of said reagent vessel 3 equipped on the upper surface of said rotation assistant body 32, and protruded in eccentricity to said recess portion 33. Furthermore, a plurality of protrusions 35 is equipped in elevation on the upper portion of the inner surface of the rotating body 21 in place of the spring material 28 of said embodiment in predetermined intervals.

Thus, the reagent vessel 3 accommodated in the rotating body 21 is eccentrically rotated by the actions of the supporting body 23 and the rotation assistant body 32. In addition, said reagent vessel 3 is made to be in contact with the protrusion body 26 mounted and elevated on said fixed gear body 25. Thus, the vessel 3 is tilted in the rotating body 21 and then shaked and agitated.

Of course, said reagent vessel 6 is held in a holding hole provided in the outside of the rotating body 21 of the fixed gear body 25 although not illustrated in FIGS. 2 through 6. A stroma solution, i.e. enzyme labeling antibody solution accommodated in said reagent vessel 6 is agitated when the fixed gear body 25 rotates.

When dividing and charging of the antibody insoluble magnetic solution into the reaction vessel 1 located at the antibody insoluble magnetic solution dividing and charging position e is thus completed, said reaction vessel 1 is conveyed towards the upstream side by a stroke equivalent to a vessel by means of the driving device. At said position, the specimen (mixed solution of the sample and the antibody insoluble magnetic solution) is agitated by the agitating device B1.

After that, said reaction vessel 1 is conveyed to a cleaning solution dividing and charging position f where a cleaning solution 5 is divided and charged into the reaction vessel 1 by means of a second pipet device P3. Said 2nd pipet device P3 comprises, similar to the composition of conventional pipet devices known in the prior art, an arm of which one end is bearingly supported onto the shaft, a pipet arranged at the other end of said arm, a pump that is connected to and communicated with said pipet and sucks a predetermined quantity of the cleaning solution 5 and discharges it into the reaction vessel 1 and each driving devices (not illustrated) that rotates and controls said arm from a predetermined position at each part to another position in a predetermined timing while controlling to lift and lower the arm at each position. The reaction vessel 1 into which the cleaning solution was divided and charged is conveyed to an enzyme labeling antibody solution dividing and charging position g where there are a first magnetic body M1 to make the antibody insoluble magnetic body m in the reaction vessel 1 onto the inner wall surface of said reaction vessel 1, a draining pipet device H1 that sucks and discards the antibody insoluble magnetic solution in the reaction vessel 1 while the antibody insoluble magnetic body m still adsorbed on the inner surface of the reaction vessel 1, a third pipet device P4 that divided and charges a stroma solution, i.e. enzyme labeling antibody solution in vessel 6 into said reaction vessel 1 after the above, and an agitating device B2 that agitates the stroma solution in vessel, i.e. enzyme labeling antibody solution 6 divided and charged in the reaction vessel 1. The third pipet device P4 comprises, referring to FIG. 7, a pipet arm 41 of which one end is bearing supported by the shaft 40, a dividing and charging pipet 42 equipped at the other end of said pipet arm 41, a pump (not illustrated) that is connected to and communicated with the dividing and charging pipet 42 and sucks a predetermined quantity of a solution and discharges it into the reaction vessel 1, and each driving device (not illustrated) that rotates and controls said pipet arm 41 from the enzyme labeling antibody solution dividing and charging position g to the enzyme labeling antibody solution suction position d through a cleaning position in predetermined timings. Measuring a quantity using said 3rd pipet device P4 is operated by filling water in the suction system and then sucks and measures the water while maintaining the water isolated from the reagent with air. Thereafter only the reagent is discharged while cleaning the inside of the pipet by flowing a cleaning water from the interior of the equipment. During such a cleaning process, the dividing and charging pipet 42 is set immediately above a trough 43 at a cleaning position i. A sample adhering on the outer surface of said dividing and charging pipet 42 is cleaned at the same position according to the composition described above.

Figures 7, 8:
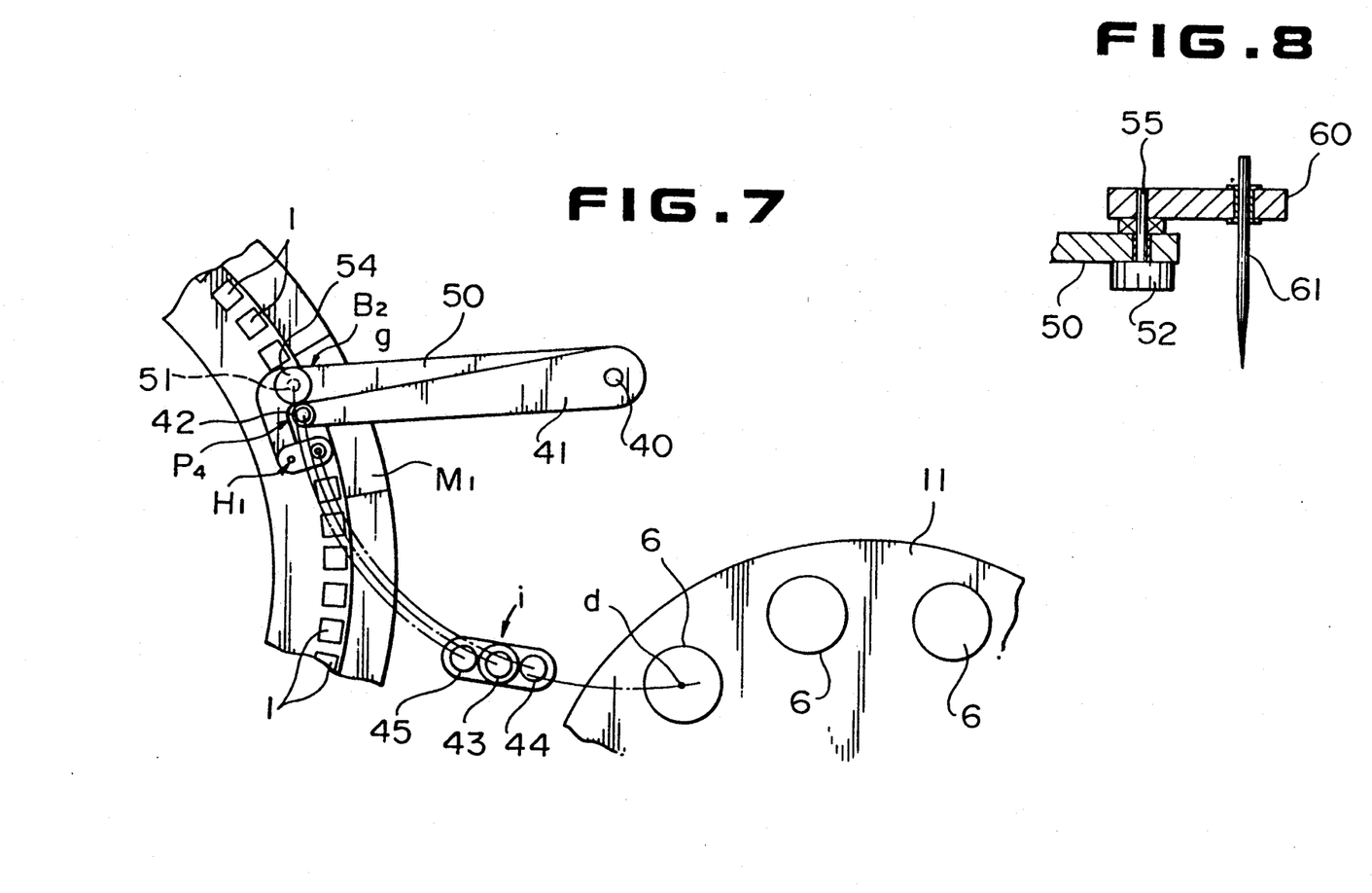
FIG. 7 is a descriptive plan view of a draining pipet device that sucks and discards an antibody insoluble magnetic solution in a reaction vessel 1 while said antibody insoluble magnetic solution still adsorbed on an inner surface of the reaction vessel by means of a first magnetic body, a third pipet device to divide and charge a stroma solution and an enzyme labeling antibody solution and an agitating device to agitate the interior of the reaction vessel 1 into which the stroma solution and the enzyme labeling antibody solution have been charged after dividing.
FIG. 8 is a section view showing the composition of the draining pipet device and the agitating device shown in FIG. 7.

Said agitating device B2 comprises, as shown in FIGS. 7 and 8, an agitating rod arm 50 shaped substantially in a planar L, an agitating body 51 arranged in an intermediate portion of said agitating rod arm 50, and a draining pipet supporting body 60 bearingly and rotatably supported at a top portion of said agitating rod arm 50 via a motor 52.

One end of the agitating rod arm 50 of said agitating device B2 is bearingly and rotatably supported by a shaft 40 that bearingly supports the pipet arm 41 of said 3rd pipet device P4.

The agitating body 51 comprises an agitating rod (not illustrated) rotated by a motor 54.

Obviously from FIG. 8, the draining pipet device H1 comprises said draining pipet supporting body 60 of which the planar shape is a long circle, said motor 52 equipped on the lower surface of the top portion of said agitating rod arm 50, a rotating shaft 55 of the motor 52, and a draining pipet 61 fixed at the other end of the draining pipet supporting body 60. Said draining pipet supporting body 60 can freely rotate around the shaft when said motor 52 revolves.

The draining pipet 61 functions in such a manner that it sucks and discards the antibody insoluble magnetic solution in said reaction vessel 1 while said magnetic body M1 still adsorbs the antibody insoluble magnetic body m in the reaction vessel 1 onto the inner surface of the reaction vessel 1 at a position in front of the enzyme labeling antibody solution dividing and charging position g. Therefore, in a normal state, the draining pipet 61 is mounted bearingly with a long axis $X_1$ of the pipet orthogonal to an axis $Y_2$ of the top portion of the agitating rod arm 50 so that the draining pipet 61 is positioned immediately above the reaction vessel 1 or a trough 44 of the cleaning position i.

Figures 9A, 9B, 9C:
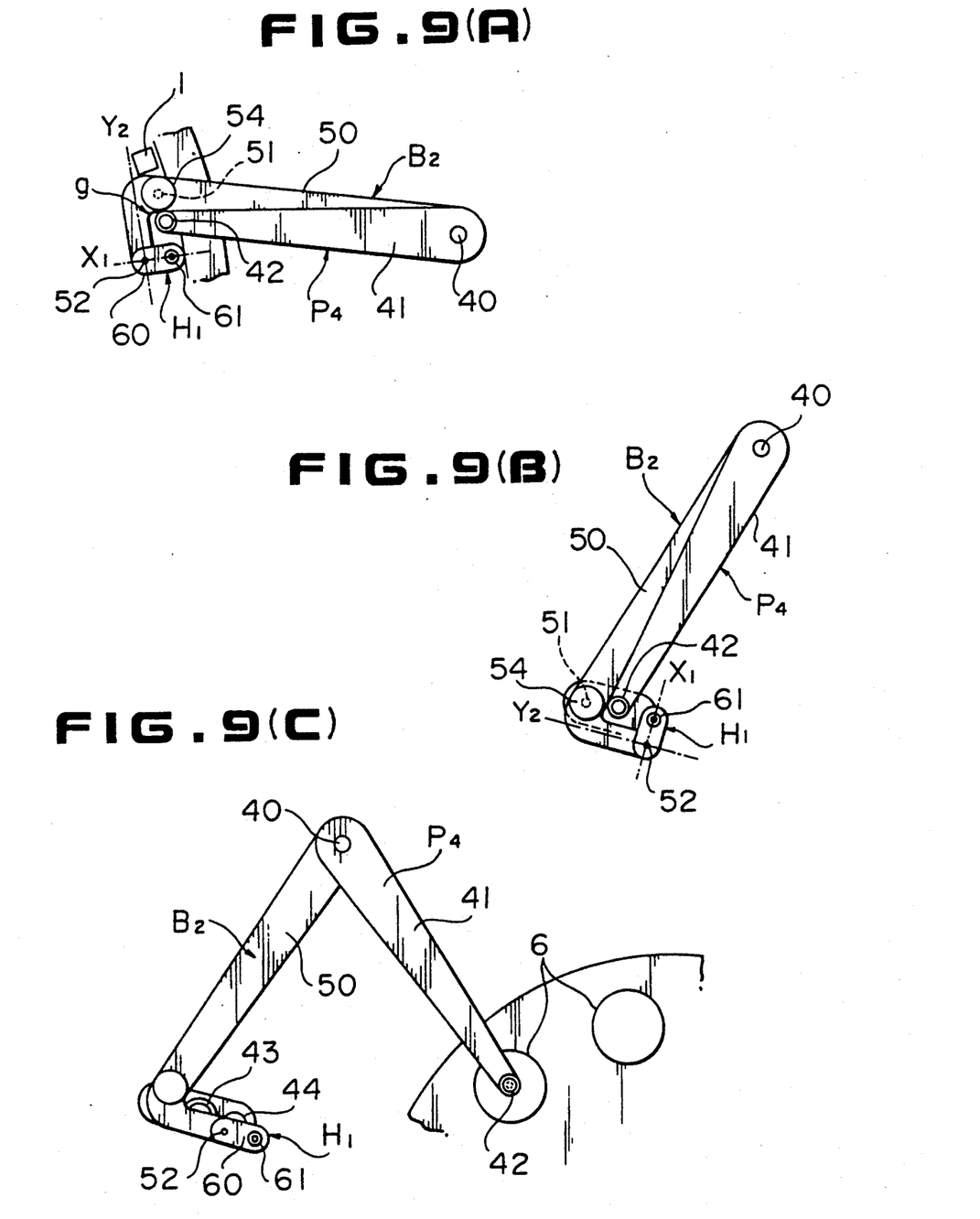

Consequently, said draining pipet supporting body 60 is pushed by the pipet arm 41 of said 3rd pipet device P4 when the 3rd pipet device P4 rotates from the position of the trough 43 to the enzyme labeling antibody solution suction position d, as shown in FIG. 9 (C). Thereby, the body 60 rotates clockwise in FIG. 9 with a supporting axis of the rotation shaft 55 of said motor 52. It is thus set in such a manner as the long axis x1 becomes in line with the axis $Y_2$ of the top portion of the agitating rod arm 50.

Thereby, the dividing and charging pipet 42 of said 3rd pipet device P4 is rotated to the enzyme labeling antibody solution suction position d without being disturbed by said draining pipet supporting body 60. At that time, the rotation shaft 55 of said motor 52 is pushed by the pipet arm 41 of the 3rd pipet device P4 since a motor switch (not illustrated) is OFF.

When the dividing and charging pipet 42 of the 3rd pipet device P4 sucks a predetermined quantity of the enzyme labeling antibody solution from the reagent vessel 6 at the enzyme labeling antibody solution suction position d and returns to said cleaning trough position, the long axis $X_1$ of said draining pipet supporting body 60 remains in a straight line with the axis $Y_2$ of the top portion of the agitating rod arm 50 until the dividing and charging pipet 42 of the 3rd pipet device P4 is set at the original position (the position shown in FIGS. 9 (A) and (B)). After the dividing and charging pipet 42 of the 3rd pipet device P4 is set at the original position, the motor 52 is turned ON since a sensor or switch (not illustrated) detects said set state, thereby rotating said draining pipet supporting body 60 to the original position (the position at which the axis $Y_2$ of the top portion of the agitating rod arm 50 becomes orthogonal to the long axis x1). The switch of the motor 52 is turned OFF thereafter. After the completion of these work processes, the pipet arm 41 of the 3rd pipet device P4, the agitating rod arm 50 of the agitating device B2 and the draining pipet supporting body 60 of the draining pipet device H1 are rotated together up to the position shown in FIG. 9 (A) and set immediately above each reaction vessel 1.

Said agitating device B2 can also be composed that air bubbles are blown for agitating in place of said agitating rod. In addition, the motor 52 can also be abolished by replacing with a spring, etc. which can reset the draining pipet supporting body 60.

Said agitating devices B1 through B6 including said agitating device B2 is composed in such a manner that the sample in the reaction vessel 1 that is located upstream by an angular stroke corresponding to each vessel from the current dividing and charging position is agitated by an agitating rod or air bubbles. These devices and tools are composed so that each pipet is cleaned at each pipet cleaning position h, i, j, k, aa and bb after the process above.

A predetermined quantity of the enzyme labeling antibody solution has been divided and charged into the reaction vessel 1 out of the reagent vessel 6 at the enzyme labeling antibody solution dividing and charging position g and then agitated as described above. After these processes, the reaction vessel 1 with said enzyme labeling antibody solution divided and charged is conveyed to a next position q where there is a magnetic body M2. As soon as the reaction vessel 1 arrives at said position q, said magnetic body M2 is energized to make the antibody insoluble magnetic body m in the reaction vessel 1 adsorbed on the inner surface of said reaction vessel 1. In addition, ingredients other than the antibody insoluble magnetic body m are drained via the cleaning and agitating device G1. A cleaning solution w is thereafter supplied into the reaction vessel 1, agitated at the next position and conveyed to a discarding position r of the sample. When the reaction vessel 1 arrives at the discarding position r after the completion of the agitating work, said magnetic body M3 is energized making the antibody insoluble magnetic body m in the reaction vessel 1 adsorbed on the inner wall surface of said reaction vessel 1. At the same time, ingredient other than the antibody insoluble magnetic body m in the sample are drained via the cleaning and agitating device G2, while supplying a cleaning solution w into the reaction vessel 1. The reaction vessel is then subject to an agitating process at a next position and then conveyed to a discarding position t of the sample. When the reaction vessel 1 thus completely agitated is conveyed to and arrives at the discarding position t, said magnetic body M4 is energized making the antibody insoluble magnetic body m in the reaction vessel 1 adsorbed on the inner wall surface of said reaction vessel 1: At the same time, ingredients other than the antibody insoluble magnetic body m in the sample are drained via the cleaning and agitating device G3 while supplying a cleaning solution w into the reaction vessel 1 which is agitated at a next position.

Figure 10:
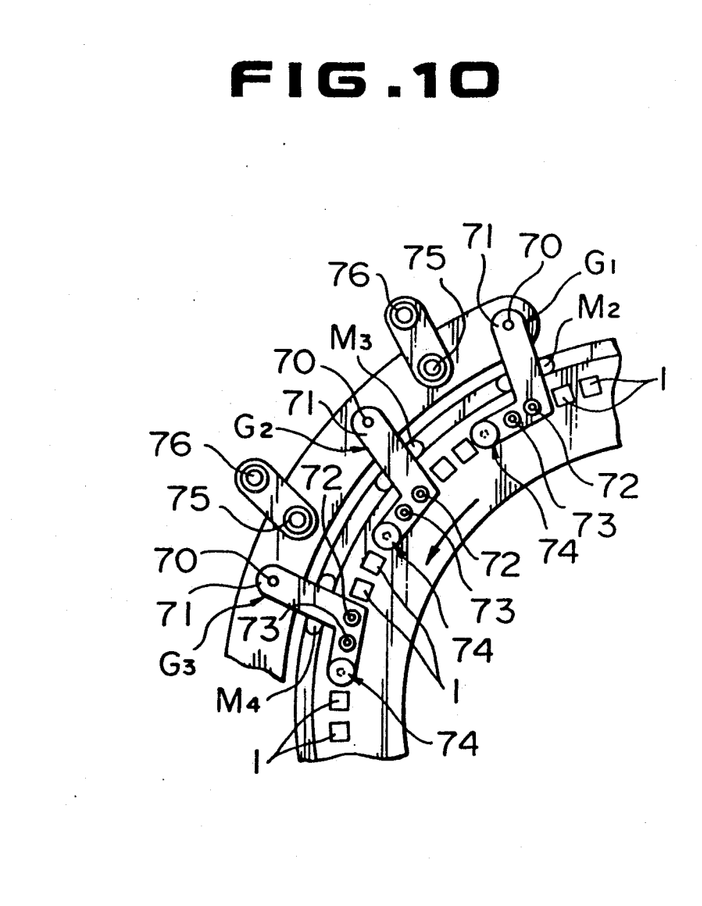
FIG. 10 is a descriptive plan view of the composition of a cleaning and agitating device.

Magnetic bodies M2 through M5 located at each position q, r and t are composed in the same way as said magnetic body M1, so no more detailed description is given herein. Said cleaning and agitating devices G1 through G3 located at each position q, r and t are composed as shown in FIGS. 10 and 11.

More explicitly, each of cleaning and agitating devices G1 through G3 comprises a plain substantial L shaped arm 71 of which one end is fixed onto the shaft 70, a solution suction pipet 72 mounted at a top portion 71a of the arm 71, a cleaning-water supplying pipet 73 and an agitating body 74.

The arm 71 is controlled to lift up and rotate by a driving device not illustrated which drives the shaft 70 which is fixed on said one end of the arm, in the same manner as conventional pipet mechanism known in the prior art. Thus, the arm 71 is composed in such a manner that it reciprocally conveys said solution suction pipet 72, cleaning water-water supplying pipet 73 and the agitating body 74 between immediately above each corresponding reaction vessel 1 and immediately above the cleaning troughs 75, 76.

The solution suction pipet 72 sucks and discards a sample in a reaction vessel 1, and is connected to and communicated with a pump (not illustrated).

The cleaning-water supplying pipet 73 supplies a cleaning water into a reaction vessel 1, of which the upper end is connected to and communicated with the pump and a cleaning water tank (not illustrated).

The agitating body 74 comprises, as particularly shown in FIG. 11, an agitating rod 78 equipped with agitating blades at the lower end and a motor 77 to rotate the agitating rod 78. Of course, in place of said agitating rod 78, the agitating body 74 may also comprise a pipe that supplies air bubbles.

Thus composed solution suction pipet 72, cleaning-water supplying pipet 73 and the agitating body 74 are installed sequentially from the downstream in the direction of conveying reaction vessels 1 into which these are inserted. Since the solution suction pipet 72, cleaning-water supplying pipet 73 and the agitating body 74 are arranged sequentially from the downstream in the direction of conveying reaction vessels 1, the antibody insoluble magnetic bodies m in reaction vessels 1 are adsorbed on the inner wall surfaces of the reaction vessels 1 by means of the magnetic bodies M2 through M5 set at each solution suction position, while sucking and discarding only unnecessary remaining samples by means of the solution suction pipets 72 and then supplying cleaning waters w into said reaction vessels. After that, said cleaning waters w and antibody insoluble magnetic bodies m are agitated by the agitating rod 78 thereby completely cleaning the antibody insoluble magnetic bodies m quickly and efficiently.

Once a work using the solution suction pipet 72, cleaning-water supplying pipet 73 and the agitating body 74 is completed in such a manner as described above, said arm 71 is rotated in the direction towards the cleaning troughs 75, 76 by said driving device while the solution suction pipet 72 and the agitating body 74 being set immediately above the cleaning troughs 75 and 76, respectively. The pipet 72, 73 and the agitating body 74 are cleaned by each cleaning device structured in the same manner as a conventional cleaning mechanism known in the prior art. After such a work as described above is completed, said solution sucking pipet 72, cleaning-water supplying pipet 73 and the agitating body 74 are conveyed again to immediately above the reaction vessels. These procedures are repeated to process samples in the reaction vessels 1 in a sequential manner.

As described above, the cleaning of the antibody insoluble magnetic bodies m is operated in 3 steps, thereby resulting in more complete cleaning effect while preventing cross contamination. However, the number of such cleaning steps may also be set freely according to the functions of an applied automatic analysis apparatus.

After completion of cleaning the antibody insoluble magnetic bodies m in such a manner as described above, said reaction vessels are conveyed to a discarding position u of the samples.

As soon as a reaction vessel 1 arrives at this sample discarding position u, said magnetic body M5 is excited making the antibody insoluble magnetic body n in the reaction vessel 1 adsorbed onto the inner wall surface of said reaction vessel 1. At the same time, ingredients other than the antibody insoluble magnetic body m are drained via a draining pipet device H2.

Thereafter, a stroma solution 7 is supplied into the reaction vessel 1 via a 4th pipet device P5 and, at the next position, it is agitated by an agitating device B3, and then, at the position after the next, a reaction stop solution is divided and charged into the reaction vessel 1 via a 4th pipet device P6.

A plurality of types (for example, 4 types in the illustrated embodiment) of reaction stop solutions are housed in reagent bottles 8 which are supported by a reagent holder 80 composed of a material preferred to see and check reagent volumes from the outside, e.g. a transparent reinforced glass or resin.

The reagent holder 80 is constructed with a substantial arc plane as shown in FIG. 1. Each of said reagent bottles 8 is inserted and held in each holding hole of which the axis is formed in predetermined pitches along a rotating locus of said 4th pipet device P5. In addition, at the top portion of said reagent holder 80, cleaning troughs 82, 83 are mounted integratedly.

The types of the reaction stop solutions, divided and charged into the reaction vessels 1 upon arriving at the reaction stop solution dividing and charging position, are entered into a control device (not illustrated) beforehand. The 4th pipet device P5 selects a reagent bottle 8 in which the specified reaction stop solution is accommodated, out of other reagent bottles 8. The pipet device P5 sucks a predetermined quantity of the reaction stop solution from the selected reagent bottle 8, and then divides and charges the sucked reaction stop solution into the reaction vessel 1.

At that time, it is preferred that these reagent holders 80 are arranged in the front side of the automatic analysis apparatus in considering easy replacing work of the reagent bottles 8.

On the other hand, the 4th pipet device P5 comprises, like a conventional reagent pipet known in the prior art, an arm 84 of which one end is supported by a shaft, a pipet 85 equipped at the other end of the arm 84, a pump (not illustrated) that is connected to and communicated with the pipet 85 and sucks a predetermined quantity of a reaction stop solution and discharges it into the reaction vessel 1 and each driving device (not illustrated) that controls said arm to rotate from a predetermined position to another position in a predetermined timing and to let the arm to go up and down at each position.

Measurement using the pipet 85 is operated as follows. A water is filled in a suction system while a reaction stop solution and the water being sucked and measured by separating them from each other via air. Only the reaction stop solution is then discharged, after which the inside of the pipet is cleaned by passing a cleaning water from the interior. During this cleaning operation, said 4th pipet device P5 is set immediately above said cleaning trough 82, where a sample adhering on the outer surface of said 4th pipet device P5 is cleaned at the same position. The agitating device B3 is conveyed according to the rotation of the arm 84 of said 4th pipet device P5. When the 4th pipet device P5 is dividing and charging a reagent into the reaction vessel 1, an agitating rod or air bubbles of the agitating device B3 agitates the sample in the reaction vessel 1 positioned in the downstream from the dividing and charging position by an angular stroke of a reaction vessel. The sample adhering on the outer surface of said agitating rod or an air bubble pipe is cleaned at the same position.

The reaction vessel 1, in which an enzyme reaction has stopped by the reaction stop solution 8, is then conveyed to an optical measuring position s. When the reaction vessel 1 arrives at said position s, said magnetic body M6 is excited to attract the antibody insoluble magnetic body m in the reaction vessel 1 in the lower part of the inner wall of said reaction vessel 1 so that it does not obstruct the optical passage of a measurement light from an optical measurement device 9.

The optical measurement device 9 comprising a detection unit or an observation point colorimetrically measures the sample in the reaction vessel 1 according to the end point method using a 400 nm and 600 nm wavelength light selected by the wavelength conversion system using a filter. A measurement data, obtained at an optical measurement position 9, is processed according to the procedures the same as those in conventional optical measuring systems and indicated on an indication device not illustrated. In addition, said data is stored in a storage IC card. On the other hand, each of said mechanisms is driven and controlled by a conventional IC card that can be read or written as known in the prior art, although not illustrated.

These storage IC card and apparatus driving IC card are provided with integrated circuits from which data can be read. These integrated circuits comprise electrically erasable programmable read only memory (EEPROM). In addition, the integrated circuits also incorporate driving and controlling means corresponding to analysis items operated in a relevant facility, in a group. In addition, the cards also store the names, registration numbers, status, affiliations and other operation information related to the operators allowed to use the relevant analysis apparatus.

On the other hand, the reaction vessels 1 are conveyed to a cleaning device F after the completion of an optical measurement work. Said cleaning device F drains all samples in the reaction vessels 1. In addition, the reaction vessels are cleaned in several stages until the inside of the reaction vessels 1 becomes reusable, using a cleaning water. The composition of the cleaning device F is the same as those of publicly known multistage cleaning devices. Therefore, no more detailed description is given herein.

In FIG. 1, a symbol Z shows a pipet cleaning position of a sampling pipet device P1.

The antibody insoluble magnetic body m is sensitized on conventional fine magnetic particles known in the prior art as an antibody. The magnetic bodies M1 through M6 making these antibody insoluble magnetic bodies m adsorbed on the inner surfaces of the reaction vessels 1 comprise electromagnets or permanent magnets and are arranged in the discarding position p, q, r, t and u of said samples and the optical measurement position s.

The operation of the embodiment in the configuration above is detailed in the following.

First, a main switch (not illustrated) is turned ON while setting the device starting IC card into the automatic immunity analysis apparatus A that has been set in an analyzable state. Thus, each mechanism is set to analyzable states while analyzed details being indicated on an indication device (not illustrated) such as a CRT. In this stage, the operator selects a preferred analysis group by pressing item switch or selective switch group (not illustrated) for a relevant examination object referring to the indication on the indication device, thereby setting an analysis unit to operate according to said selected analysis items.

Next, when a start switch (not illustrated) is turned ON in the state above, thus, the sample cassette 12 conveys each sample vessel 10 to a sample suction position b intermittently, at which the sampling pipet device P1 sucks a sample. Thereafter, said sampling pipet device P1 rotates to divide and charge the sucked sample into the reaction vessel 1 by, for example, 10~100 μM. After the completion of the work above, the reaction vessels 1 are rotated by an angular stroke corresponding to 71 vessels (355°) counterclockwise in FIG. 1, and stopped. As a result, said reaction vessels 1 are intermittently conveyed by an angular stroke of 1 reaction vessel clockwise in FIG. 1. After that, the reaction vessels 1 are conveyed sequentially and intermittently in the intervals of the angular stroke corresponding to each reaction vessel clockwise in FIG. 1.

The process sequencing detailed in FIGS. 12-34 will now be described. When the reaction vessels 1 are fed from the sampling position "a" to the solution antibody insoluble magnetic solution dividing and charging position e, the solution antibody insoluble magnetic solution is divided and charged into each reaction vessel 1 by means of the 1st pipet device P2. At the next position, the solution is agitated by the agitating device B1. After this step, a cleaning solution 5 is divided and charged into each of said reaction vessels 1 at a position f.

The reaction vessels 1 with cleaning solutions 5 additionally divided and charged are conveyed to a position p where the 1st magnetic body M1 is arranged and, when the reaction vessel 1 arrives at said position p, said 1st magnetic body M1 is energized making the antibody insoluble magnetic body m in the reaction vessel 1 is adsorbed on the inner wall surface of said reaction vessel 1. In addition, ingredients other than the antibody insoluble magnetic body m are drained via a draining pipet device H1.

When this work is completed with the reaction vessels, the vessels are conveyed next to an enzyme labeling antibody solution dividing and charging position g where a stroma solution, i.e. an enzyme labeling antibody solution is divided and charged via a 3rd pipet device P4 by a predetermined quantity. At the next position, the solution in the reaction vessel 1 is agitated by an agitating device B2.

The reaction vessels 1, thus charged with the stroma solution, i.e. the enzyme labeling antibody solution after dividing, are conveyed to the next position q where the magnetic body M2 is located. When the reaction vessels 1 arrive at said position q, said magnetic body M2 is excited making the antibody insoluble magnetic body m in the reaction vessel 1 adsorbed on the inner wall surface of said reaction vessel 1. In addition, samples other than the antibody insoluble magnetic body m are drained. After that, a cleaning solution w is supplied into the reaction vessel 1. At the next position, the solution w is agitated while conveying the reaction vessels to a sample discarding position r.

The reaction vessels 1, thus completely agitated, are conveyed to the discarding position r and, when the reaction vessels 1 arrive at said position r, said magnetic body M3 is energized making the antibody insoluble magnetic body m in the reaction vessel 1 adsorbed on the inner wall surface of said reaction vessel 1. In addition, samples other than the antibody insoluble magnetic body m are drained, after which a cleaning solution w is supplied into the reaction vessels 1. At the next position, the reaction vessels are agitated and then conveyed to a sample discarding position t.

When the reaction vessels 1, after being completely agitated in such a manner as described above, are conveyed to the discarding position t and arrives thereat, said magnetic body M4 is excited making the antibody insoluble magnetic body m in the reaction vessel 1 adsorbed on the inner wall surface of said reaction vessel 1. In addition, samples other than the antibody insoluble magnetic body m are drained. After this step, a cleaning solution w is supplied into the reaction vessel 1 and, at the next position, the solution w is agitated while then conveying the reaction vessels to a sample discarding position u.

When thus completely agitated reaction vessels 1 is conveyed to a discarding position u and arrives at there, said magnetic body M5 is energized making the antibody insoluble magnetic body m in the reaction vessel 1 adsorbed on the inner wall surface of said reaction vessel 1. Also, samples other than the antibody insoluble magnetic body m are drained via the discharging pipet device H2. After this, a stroma solution 7 is supplied into the reaction vessel 1 via the 4th pipet device P5. The solution 7 is agitated at the next position by means of an agitating device $B_2$. At the position after the next, a reaction stop solution 8 is divided and charged into the reaction vessel 1 via a 5th pipet device P6.

The reaction vessels 1, in which an enzyme reaction has been stopped by the reaction stop solution 8 in the manner described above, are conveyed to an optical measurement position s and, when the reaction vessels 1 arrive at said position s, said magnetic body M6 is energized making the antibody insoluble magnetic body m in the reaction vessel 1 adsorbed on the lower side of the inner wall of said reaction vessel 1 so that an optical passage f of a measuring right from the optical measurement device 9 is not obstructed.

Thus, a data measured by the optical measurement device 9 is processed and calculated according to said procedures and indicated on an indication device not illustrated. In addition, said data is stored in a storage IC card. On the other hand, the reaction vessels 1 completely passed through the optical measurement work are conveyed to a cleaning device F which drains all samples in the reaction vessels 1. In addition, the reaction vessels 1 are cleaned with a cleaning water in multiple stages until the vessels can be reused.

In the embodiment above, such a composition as the activation of the automatic immunity analysis apparatus A is controlled by a starting IC card has been used for an explanation. However, the present invention is not restricted only to such a composition but applicable also to an automatic immunity analysis apparatus activated by another control means known in the prior art.

In this embodiment, the cleaning solution 5 is divided and charged at the position f using the 2nd pipet device P3 and then, at the position p, the 1st magnetic body M1 is energized to make the antibody insoluble magnetic body m adsorbed on the inner wall surface of the reaction vessel 1 together with draining samples other than the antibody insoluble magnetic body m using the draining pipet device H1, according to a 2-step method used in the automatic immunity analysis apparatus A, as an example. However, the present invention is also not restricted only to such an arrangement. Instead, such an automatic immunity analysis apparatus A in 1-step system can also be embodied, that a stroma solution, i.e. an enzyme labeling antibody solution is divided and charged at a position g after the completion of the dividing and agitating work of the solution antibody insoluble magnetic solution by omitting said 2-step processes.

FIELD OF INDUSTRIAL APPLICATIONS

According to the present invention as described and detailed above, an insoluble antibody in which an antibody is fixed onto fine magnetic particles is used in the enzyme immunity measurement using the EIA method. Therefore, the time required to clean said antibody can be greatly simplified and shortened. As a result, the time of such an inspection can significantly be reduced while totally automating a series of works such as sampling, dividing and charging of a reagent, agitating, cleaning and measuring. Thus, the present invention provides a completely novel and excellent automatic immunity analysis apparatus better than conventional apparatuses known in the prior art, because the invented apparatus makes these types of inspections completely automated.

What is claimed is:

1. An automatic immunity analysis apparatus comprising reaction vessels arranged in a series, a conveying means for said reaction vessels, a first dividing means for sucking a sample in a predetermined quantity at a predetermined position and dividing and charging said sample into each of said reaction vessels, a first agitating means for dividing, charging and agitating an antibody insoluble magnetic solution into each of said reaction vessels containing said sample divided and charged, a second dividing means which is positioned after said first agitating means, said second dividing means for dividing and charging a stroma solution into each of said vessels, a first adsorbing means for adsorbing said antibody insoluble magnetic solution onto an inner wall surface of each of said reaction vessels, a first cleaning means for discarding a reactions solution out of each of said reaction vessels while said antibody insoluble magnetic solution is still adsorbed on the inner wall of each of said reaction vessels and then cleaning each of said vessels, a second agitating means for dividing and agitating an enzyme labeling antibody solution, a second absorbing means for adsorbing said antibody insoluble magnetic solution onto an inner wall surface of each of said reaction vessels, a second cleaning means for discarding a reaction solution out of each of said reaction vessels while said antibody insoluble magnetic solution is still adsorbed on the inner wall of each of said reaction vessels and then cleaning each of said vessels, a third dividing means for dividing and charging a reaction stop solution, a measuring means for optically measuring a sample in each of said reaction vessels at an optical measuring position, and a third cleaning means for cleaning the inside of each of said reaction vessels after completion of a measurement, wherein said first dividing means, said first agitating means, said second dividing means, said first adsorbing means, said first cleaning means, said second agitating means, said second absorbing means, said second cleaning means, said third dividing means, said measuring means and said third cleaning means are arranged sequentially beginning with said first dividing means and ending with said third cleaning means on said conveying means in said automatic immunity analysis apparatus, wherein said first agitating means further comprises a reagent vessel holder which is rotated by means of a driving apparatus, a rotating body which is engaged with a retention hole of said reagent vessel holder in a freely rotatable manner and has an aperture in a side surface, a fixed gear body having a first peripheral surface of which gear teeth are cut thereon, said fixed gear body mounted on said reagent vessel holder, a gear body which engages with the gear teeth of said fixed gear body and drives said rotating body when said reagent vessel holder rotates, said fixed gear body further including protrusion bodies which are elevated in predetermined intervals along a second peripheral surface of said fixed gear body, said protrusion bodies extending through said aperture during driving of said rotation body, wherein an antibody insoluble magnetic solution accommodated in said rotating body is rotated and agitated when said reagent vessel holder revolves, and accommodated in said rotating body in such a manner that said reagent antibody insoluble magnetic solution is shaken and agitated by one of said protrusion bodies extending through said aperture.

2. The automatic immunity analysis apparatus specified in claim 1, wherein each of said first and second cleaning means further comprise an arm having a substantially L-shaped configuration fixed onto a shaft at an end thereof, a solution suction pipet arm, a cleaning-water supplying pipet and an agitating body;

said solution suction pipet, said cleaning-water supplying pipet and said agitating body being mounted at a top portion of a said arm in a sequential order as from a downstream side to an upstream side in the direction of conveying the reaction vessels into which each of said solution suction and cleaning-water supplying pipets and said agitating body are inserted.

3. An automatic immunity analysis apparatus comprising reaction vessels arranged in a series, a conveying means for said reaction vessels, a first dividing means for sucking a sample in a predetermined quantity at a predetermined position and dividing and charging said sample into each of said reaction vessels, a first agitating means for dividing, charging and agitating an antibody insoluble magnetic solution into each of said reaction vessels containing said sample divided and charged, a second dividing means which is positioned after said first agitating means, said second dividing means for dividing and charging a stroma solution into each of said vessels, a first adsorbing means for adsorbing said antibody insoluble magnetic solution onto an inner wall surface of each of said reaction vessels, a first cleaning means for discarding a reaction solution out of each of said reaction vessels while said antibody insoluble magnetic solution is still adsorbed on the inner wall of each of said reaction vessels and then cleaning each of said vessels, a second agitating means for dividing and agitating an enzyme labeling antibody solution, a second adsorbing means for adsorbing said antibody insoluble magnetic solution onto an inner wall surface of each of said reaction vessels, a second cleaning means for discarding a reaction solution out of each of said reaction vessels while said antibody insoluble magnetic solution is still adsorbed on the inner wall of each of said reaction vessels and then cleaning each of said vessels, a third dividing means for dividing and charging a reaction stop solution, a measuring means for optically measuring a sample in each of said reaction vessels at an optical measuring position, and a third cleaning means for cleaning the inside of each of said reaction vessels after completion of a measurement, wherein said first dividing means, said first agitating means, said second dividing means, said first adsorbing means, said first cleaning means, said second agitating means, said second absorbing means said second cleaning means, said third dividing means, said measuring means and said third cleaning means are arranged sequentially beginning with said first dividing means and ending with said third cleaning means on said conveying means in said automatic immunity analysis apparatus, wherein said first agitating means further comprises an agitating rod arm having a substantially L-shaped configuration and a pipet arm, where said agitating rod arm is equipped with an agitating body at an intermediate portion and a draining pipet supported by a draining pipet body, said draining pipet body supported on a bearing at a top and end portion of said agitating rod arm, and said pipet arm is equipped with a dividing pipet at an end portion, wherein said agitating rod arm and said pipet arm are supported by a shaft, said shaft rotatably supporting said agitating rod arm and bearingly supporting said pipet arm and means for rotating said pipet arm independently of said agitating arm and for pushing said draining pipet body out of place; wherein said agitating rod arm, said draining pipet and said dividing pipet are cleaned at a predetermined position; then only said dividing pipet rotates while pushing the draining pipet and draining pipet body out of place, said dividing pipet moving to a solution sucking position; and said draining pipet returning back in place when said dividing pipet sucks the antibody insoluble magnetic solution and returns back to said predetermined cleaning position.

4. The automatic immunity analysis apparatus specified in claim 3, wherein each of said first and second cleaning means further comprise an arm having a substantially L-shaped configuration fixed onto a shaft at an end thereof, a solution suction pipet arm, a cleaning-water supplying pipet and an agitating body;

said solution suction pipet, said cleaning-water supplying pipet and said agitating body being mounted at a top portion of a said arm in a sequential order as from a downstream side to an upstream side in the direction of conveying the reaction vessels into which each of said solution suction and cleaning-water supplying pipets and said agitating body are inserted.

* * * * *